US009226674B2

(12) United States Patent
Vellani et al.

(10) Patent No.: US 9,226,674 B2
(45) Date of Patent: Jan. 5, 2016

(54) VECTOR-CARDIO-GRAPHIC SIGNAL ANALYZER

(71) Applicants: Cameruddin Walimuhammad Vellani, Karachi (PK); Mohammad Yusuf, Karachi (PK); Sadia Mahmud, Islamabad (PK)

(72) Inventors: Cameruddin Walimuhammad Vellani, Karachi (PK); Mohammad Yusuf, Karachi (PK); Sadia Mahmud, Islamabad (PK)

(73) Assignee: The Aga Khan University, Karachi (PK)

( * ) Notice: Subject to any disclaimer, the term of this patent is extended or adjusted under 35 U.S.C. 154(b) by 0 days.

(21) Appl. No.: 13/972,654

(22) Filed: Aug. 21, 2013

(65) Prior Publication Data

US 2015/0005651 A1 Jan. 1, 2015

(30) Foreign Application Priority Data

Jun. 26, 2013 (PK) .................................... 429/2013

(51) Int. Cl.
*A61B 5/04* (2006.01)
*A61B 5/0452* (2006.01)
*A61B 5/0432* (2006.01)
*A61B 5/00* (2006.01)
*A61B 5/0472* (2006.01)
*A61B 5/0456* (2006.01)
*A61B 5/044* (2006.01)

(52) U.S. Cl.
CPC ........... *A61B 5/04011* (2013.01); *A61B 5/0006* (2013.01); *A61B 5/0022* (2013.01); *A61B 5/04012* (2013.01); *A61B 5/0456* (2013.01); *A61B 5/0472* (2013.01); *A61B 5/7246* (2013.01); *A61B 5/044* (2013.01)

(58) Field of Classification Search
None
See application file for complete search history.

(56) References Cited

U.S. PATENT DOCUMENTS

| 4,216,780 | A  | * | 8/1980 | Rubel et al. ................... 600/512 |
| 6,115,630 | A  | * | 9/2000 | Stadler et al. ................. 600/521 |
| 8,626,266 | B1 | * | 1/2014 | Frank et al. ................... 600/413 |
| 2003/0083587 | A1 | * | 5/2003 | Ferek-Petric ................. 600/512 |
| 2005/0209525 | A1 | * | 9/2005 | Bojovic et al. ................ 600/512 |
| 2010/0249622 | A1 | * | 9/2010 | Olson ........................... 600/509 |

* cited by examiner

*Primary Examiner* — Brian T Gedeon
(74) *Attorney, Agent, or Firm* — Mintz Levin Cohn Ferris Glovsky and Popeo, P.C.

(57) ABSTRACT

The current subject matter relates to indicating extent and location of myocardial ischemia in a patient. Electrodes can be placed on a body of the patient. Signal amplifiers can receive orthogonal electrical signals from the electrodes via three bipolar leads. The signal amplifiers can amplify the signals and send the amplified signals to analog to digital converters. The analog to digital converters can convert the amplified signals to digital signals. A computing device can execute a data analysis application that can receive these digital signals, generate QRS complexes associated with these signals, generate depolarization vectors associated with these QRS complexes, and then determine changes in magnitudes and directions of these vectors. Based on the changes in magnitudes and directions, the data analysis application can determine and display extent and location of myocardial ischemia in the patient. Related apparatus, systems, methods, techniques and articles are also described.

8 Claims, 13 Drawing Sheets

| e8.5 | Summary | | P16 | | | | | e8.5 | Summary | | P16 | | | | |
|---|---|---|---|---|---|---|---|---|---|---|---|---|---|---|---|
| Depol time ms | RVM +ve score | RVM -ve score | Structures in the main spatial directions of reduced RVM | Areas in the lesser spatial directions of reduced RVM | Location of reduced EMF from change in vector direction | Lesser spatial location of reduced EMF | Score change in average vector direction | Depol time ms | RVM +ve score | RVM -ve score | Structures in the main spatial directions of reduced RVM | Areas in the lesser spatial directions of reduced RVM | Location of reduced EMF from change in vector direction | Lesser spatial location of reduced EMF | Score change in average vector direction |
| 1.5 | | -5 | IVS | Superior | A | R | 5 | 43.5 | 1 | | | | | | |
| 3 | | -5 | IVS | Superior | A | R | 4 | 45 | 1 | | | | | | |
| 4.5 | | -4 | IVS | Superior | A | R | 3 | 46.5 | | | | | | | |
| 6 | | -3 | IVS | Superior | A | R | 2 | 48 | | | | | | | |
| 7.5 | | -2 | IVS | Superior | A | R | 2 | 49.5 | | | | | | | |
| 9 | | -2 | IVS | Superior | A | R | 2 | 51 | | | | | | | |
| 10.5 | | -1 | IVS | Superior | A | R | 2 | 52.5 | | -1 | Lat-inf LV | Posterior | | | 1 |
| 12 | | -1 | IVS | Superior | A | | 1 | 54 | | -1 | Lat-post LV | Inferior | | | 3 |
| 13.5 | | -23 | | | | | 1 | 55.5 | | -2 | Lat-post LV | Inferior | | | 3 |
| 15 | 1 | | | | | | | 57 | | -2 | Lat-post LV | Inferior | | | 3 |
| 16.5 | 1 | | | | | | 1 | 58.5 | | -2 | Post-lat LV | Superior | | | 3 |
| 18 | 1 | | | | | | 2 | 60 | | -8 | | | | | 3 |
| 19.5 | 1 | -2 | ant-sup IVS | Left-lateral | L | S | 5 | 61.5 | 1 | | | | L | P | 4 |
| 21 | | -5 | Ant-lat LV | Superior | L | A | 5 | 63 | 3 | | | | | | 4 |
| 22.5 | | -4 | Lat-ant LV | | L | A | 1 | 64.5 | 4 | | | | | | 5 |
| 24 | | -3 | Lat-ant LV | Inferior | | | | 66 | 5 | | | | | | 5 |
| 25.5 | | -2 | Lat-ant LV | Inferior | | | | 67.5 | 5 | | | | | | 5 |
| 27 | | -1 | Lat-ant LV | Inferior | | | | 69 | 5 | | | | | | 5 |
| 28.5 | | -1 | Lat-ant LV | Inferior | | | | 70.5 | 5 | | | | | | 5 |
| 30 | | -1 | Lat-ant LV | Inferior | | | | 72 | 5 | | | | | | 5 |
| 31.5 | | -19 | | | | | | 73.5 | 5 | | | | | | 5 |
| 33 | | | | | | | | 75 | 5 | | | | | | 5 |
| 34.5 | | | | | | | | 76.5 | 5 | | | | | | 5 |
| 36 | | | | | | | | 78 | 5 | | | | | | 5 |
| 37.5 | | | | | | | | Sum | 59 | -50 | | | | | 89 |
| 39 | | | | | | | | | | | | | | | |
| 40.5 | | | | | | | | | | | | | | | |
| 42 | | | | | | | | | | | | | | | |

VECTOR-CARDIO-GRAPHIC SIGNAL ANALYZER

RELATED APPLICATION

The current patent application claims priority to Pakistan Patent Application No. 429/2013, filed on Jun. 26, 2013, and entitled "Vector-Cardio-Graphic Signal Analyzer", the contents of which are hereby fully incorporated by reference.

TECHNICAL FIELD

The subject matter described herein relates to a vector-cardio-graphic signal analyzer for determining a problem of change in a functionality of the heart in the body of a patient, and determining the location of the change. More specifically, the vector-cardio-graphic signal analyzer determines an extent and a location of myocardial ischemia in the body of the patient.

BACKGROUND

Conventionally, myocardial perfusion scans are known for identifying myocardial ischemia in a patient, and the location of myocardial ischemia in the body of the patient. A myocardial perfusion scan includes images of the heart that characterize change in blood supply to a heart muscle of the patient during peak exercise relative to rest. To obtain a myocardial perfusion scan, a clinician injects a radioactive tracer into a vein of an arm of the patient. The radioactive tracer travels through the blood and into the heart muscle. As the tracer moves through the heart muscle, areas that have a good blood flow absorb the tracer, and areas that have reduced blood flow (for example, either restricted by a narrow artery or damaged by a closure causing a heart attack) absorb less of the tracer. A myocardial perfusion scan imaging device includes a camera that takes pictures of radioactivity distributed in the heart muscle. These pictures enable inference of the paths of the radioactive tracer and extent of the areas that do not have a good blood flow.

Although a myocardial perfusion scan imaging device can be used to identify myocardial ischemia and a location of the myocardial ischemia, these imaging devices are expensive and immobile. Further, the imaging results are dependent on technical skills of the operators and expertise of the interpreter that can lead to misinterpretation of images. Moreover, the test requires protection of the environment and persons exposed to radiation from the tracer during handling, international transport for delivery and use at a specially constructed site.

SUMMARY

The current subject matter describes a system for indicating extent and location of myocardial ischemia in a patient. Electrodes can be placed on a body of the patient. Signal amplifiers can receive orthogonal electrical signals from the electrodes via three bipolar leads. The signal amplifiers can amplify the signals and send the amplified signals to analog to digital converters. The analog to digital converters can convert the amplified signals to digital signals. A computing device can execute a data analysis application that can receive these digital signals, generate QRS complexes associated with these signals, generate depolarization vectors associated with the generated QRS complexes, and then determine changes in magnitudes and directions of these vectors. Based on the changes in magnitudes and directions, the data analysis application can determine and display extent and location of myocardial ischemia in the patient. Related apparatus, systems, methods, techniques and articles are also described.

In one aspect, a system can include an analog to digital converter and a computing device. The analog to digital converter can receive electrical signals recorded using a plurality of electrodes attached to a body of a patient. The analog to digital converter can convert the electrical signals to digital signals. The computing device can analyze the digital signals to generate an indication characterizing extent and location of myocardial ischemia in the body of the patient.

In some variations, one or more of the following can be implemented individually or in any feasible combination. The system can further include one or more lead signal amplifiers to receive electrical signals recorded using the plurality of electrodes. The one or more lead signal amplifiers can amplify the electrical signals by filtering out high frequency components of the electrical signals by using one or more low pass filters. The one or more lead signal amplifiers can send the amplified digital signal to the analog to digital converter. The one or more lead amplifiers can obtain the electrical signals via a first bipolar lead, a second bipolar lead, and a third bipolar lead. The first bipolar lead can transmit an electrical signal of a horizontal plane of three orthogonal planes. The second bipolar lead can transmit an electrical signal of a frontal plane of the three orthogonal planes. The third bipolar lead can transmit an electrical signal of a sagittal plane of the three orthogonal planes.

The system can further include a database to store the digital signals obtained from the analog to digital converter. The computing device can receive the stored digital signals from the database to analyze the digital signals. The database can obtain the digital signals from the analog to digital converter via a first communication network.

The computing device can receive the stored digital signals via a second communication network. The computing device can execute a graphical user interface that can display the indication characterizing an extent and location of myocardial ischemia in the body of the patient.

The analyzing of the digital signals by the computing device can be performed as follows. The digital signals associated with three orthogonal planes can be received. Using the digital signals and first derivatives of the digital signals, a QRS complex for each orthogonal plane can be generated. Average QRS complexes for each orthogonal plane can be determined. A plurality of planar vectors characterizing the average QRS complexes can be generated. Planar vectors associated with each stage of a plurality of stages of exercise of the patient can be aligned. Changes in magnitudes and directions of the planar vectors associated with different stages of exercise can be determined. The indication can characterize extent and location of myocardial ischemia that is generated based on the changes in magnitudes and directions of vectors.

In another aspect, a data analysis application executed on a computing device can receive digital lead signals characterizing a digitized form of lead signals obtained from a plurality of leads connected to electrodes attached on a body of a patient. The lead signals can characterize components of a collective signal in corresponding orthogonal planes. The data analysis application can construct QRS complexes associated with the corresponding orthogonal planes by using the digital lead signals. The data analysis application can generate planar vectors associated with averages of the QRS complexes. The data analysis application can display an indication characterizing extent and location of myocardial ischemia in the body of the patient on a graphical user interface executed by the computing device. The indication can be generated based on changes in magnitudes and directions of the planar vectors during different stages of activity of the patient.

In some variations, one or more of the following can be implemented individually or in any feasible combination. The construction of the QRS complexes can include: receiving a digital lead signal of the lead signals; generating a first differential of the lead signal; removing high frequency noise from the lead signal by using a low pass filter to obtain a smooth first differential; and simultaneously displaying the digital lead signal and the first differential to identify parameters of the QRS complex associated with the digital lead signal, the parameters being used to construct the QRS complex. A positive peak of the smooth first differential can identify an upward slope of R wave in the QRS complex associated with the digital lead signal. Attainment of zero value of the first differential in transition to a negative trough can identify a peak of the R wave in the QRS complex. A negative trough of the first differential can identify a downward slope of the R wave in the QRS complex.

The averages of the QRS complexes can be obtained by performing an averaging of the QRS complexes. The averaging can include: calculating a baseline characterizing a mean value of sample points of PR segment preceding each QRS complex; adjusting a digital lead signal of the lead signals with reference to the baseline to obtain a baseline adjusted lead signal; separately cross-correlating the baseline adjusted lead signal with a plurality of lead signals in subsequent windows of analysis, each cross-correlation resulting in a sum of products of values of the baseline adjusted lead signal and a corresponding lead signal of a subsequent window of analysis; determining, from the plurality of lead signals in subsequent windows of analysis, a lead signal that has a highest sum of corresponding products, the determined lead signal with the highest sum of corresponding products being more similar to the baseline adjusted lead signal than other lead signals; and averaging a QRS complex associated with the baseline adjusted lead signal and a QRS complex associated with the determined lead signal with the highest sum of corresponding products when the QRS complex associated with the determined lead signal is determined to be a regular waveform.

The generating of the indication of extent and location of myocardial ischemia can include generating of a relative vector magnitude at each depolarization time point at a first time since the patient started an exercise. The relative vector magnitude can be a ratio of vector magnitude at the first time to the vector magnitude before exercise. The generating of the indication can further include using criteria to generate an indication that the patient has ischemia.

In yet another aspect, a non-transitory computer program product is described. The computer program product can store instructions that, when executed by at least one programmable processor, can cause the at least one programmable processor to perform the following operations. A data analysis application executed on a computing device can receive digital lead signals characterizing a digitized form of lead signals obtained from a plurality of leads connected to electrodes attached on a body of a patient. The lead signals can characterize components of a collective signal in corresponding orthogonal planes. The data analysis application can construct QRS complexes associated with the corresponding orthogonal planes by using the digital lead signals. The data analysis application can generate planar vectors associated with averages of the QRS complexes. The data analysis application can display, on a graphical user interface executed by the computing device, an indication characterizing extent and location of myocardial ischemia in the body of the patient. The indication can be generated based on changes in magnitudes and directions of the planar vectors during different stages of activity of the patient.

The subject matter described herein can also be implemented on computer systems that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The subject matter described herein provides many advantages. For example, the current subject matter for determining the extent and location of myocardial ischemia can be a reliable and more-effective alternative to myocardial perfusion scans. Moreover, the system is inexpensive as compared to conventional systems. Further, the system is portable, and can be easily moved from one location to another distant location. Furthermore, this system determines the extent and location of myocardial ischemia without inserting any foreign substance (for example, radioactive tracer) into the body of the patient, thereby allowing a safe and a non-invasive determining. Additionally, the system relies on a vector based approach that has been experimented on historical data of many patients, thereby generating the potential for a reliable determination of extent and location of myocardial ischemia.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 13 is a diagram illustrating indications of extent, duration, and spatial direction of vectors that are reduced in magnitude.

Like reference symbols in the various drawings indicate like elements.

DETAILED DESCRIPTION

Human body includes a Purkinje network, which is a complex fibrous network of large muscle cells that spread depolarising electrical potentials rapidly through the right and left ventricles of the heart just beneath an innermost lining of the ventricles. These electrical potentials trigger mechanical contraction of the heart muscle. The sequences, mass, and distribution of rapidly progressive depolarization produce first electrical vectors. The components of these first electrical vectors in orthogonal planes (for example, horizontal plane, frontal plane, and sagittal plane) can be obtained using respective leads. When the blood flow to the heart muscles and Purkinje network is reduced, insufficient oxygen is available for the heart muscles and the Purkinje network relative to their work. Then, the cellular excitability and the depolarization of those structures are reduced. Slowing of the depolarization alters the synchrony of forces causing the formation of first electrical vectors. This altered synchrony of forces can result in formation of second electrical vectors, at least one of magnitude and direction of which are different from the magnitude and direction of the first electrical vectors. Such changes in at least one of the magnitude and direction of electrical vectors, and the sequence of such changes, can be used to diagnose extent and location of myocardial ischemia. Myocardial ischemia is a health problem where insufficient blood flows through blood vessels delivering blood to the heart muscle.

Figure 1:
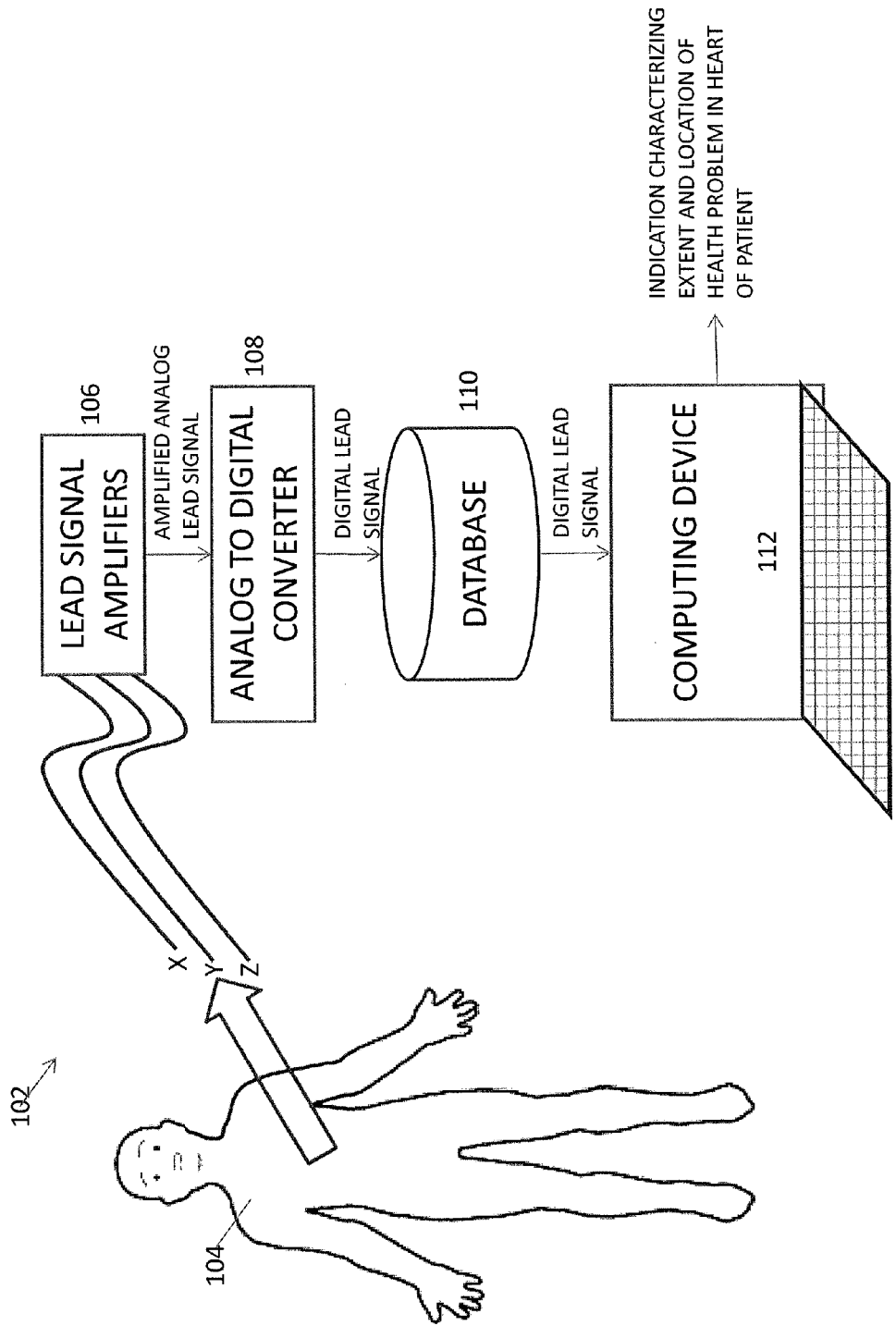
FIG. 1 is a diagram illustrating a system for detecting extent and location of a perfusion related health problem in the heart of a patient.

FIG. 1 is a diagram 100 illustrating a system 102 for detecting extent and location of a health problem (for example, a perfusion related problem) in a heart of a patient 104. The health problem can be myocardial ischemia.

A clinician can place electrodes on the arms, legs, and/or chest of the patient 104. The electrodes can detect electrical impulses produced every time the heart beats via the skin. The clinician can use a template to determine locations of electrodes on the skin of the patient 104. The template can include a stiff plastic sheet with holes where the clinician can place the electrodes. The clinician can place this template sheet on the body of the patient 104 by using a reference point that can be a fifth intercostal space in the body of the patient 104. The fifth intercostal space can be two centimeters from the left sternal border. To facilitate bonding between the skin of the patient 104 and the electrodes, the clinician can de-grease the skin of the patient 104 that can minimize electrical resistance. Further, the electrodes can include adhesive collars that can minimize slippage of the electrodes. In one implementation, the clinician can place ten electrodes on the torso of the patient 104.

The electrodes can measure three orthogonal lead signals in respective orthogonal planes (for example, horizontal plane, frontal plane, and sagittal plane) during different stages of activity of the patient 104. The different stages of activity can include rest and different stages of exercise. The different stages of exercise can correspond to different times since the patient 104 begins the exercise. The electrodes can transmit the orthogonal lead signals via three independent bipolar leads X, Y, and Z. The three bipolar leads X, Y, and Z can be located as follows.

X bipolar lead: From the point of reference in a same transverse plane, a point can be marked in a left lateral position. This point can be one third of the distance from the anterior to posterior chest surfaces. Two electrodes can be placed eleven centimeters apart and centered on the lateral point of the transverse plane constitute the positive terminal of the X bipolar lead. The negative terminal of the X bipolar lead can include one electrode that can be symmetrically opposite on the right lateral chest.

Y bipolar lead: The positive terminal of the Y bipolar lead can include an electrode five centimeters below the umbilicus, and the negative terminal of the Y bipolar lead can include an electrode placed medially above the left clavicle in the same vertical line. The positive terminal of the Y bipolar lead can be placed approximately five centimeters below the umbilicus in line with the negative terminal of the Y bipolar lead to minimize muscle potentials.

Z bipolar lead: The positive terminal of the Z bipolar lead can have three electrodes at corners/angles of an equilateral triangle. Each side of the equilateral triangle can be six centimeters long. The apex of the equilateral triangle can be vertically upwards towards the head of the patient 104. Each corner/angle of the equilateral triangle can be equidistant from the point of reference. The negative terminal of the Z bipolar lead can have one electrode placed directly posterior to the point of reference in the same transverse plane.

A ground electrode, which can be connected to the ground, can be attached to the right abdominal skin.

The electrodes on the body of the patient 104 can transmit the orthogonal lead signals to three signal amplifiers 106 via the three independent bipolar leads X, Y, and Z, respectively. Each signal amplifier 106 can amplify the corresponding orthogonal lead signal. In one implementation, one or more signal amplifiers 106 can be Coulbourn Instruments isolated Bioamplifiers V75-04 that can be set for low pass filtration at one hundred and fifty hertz.

The lead signal amplifiers 106 can send the three separately amplified lead signals to an analog to digital converter 108. The analog to digital converter 108 can convert the amplified lead signals to digital lead signals at regular intervals of time, such as regular intervals of 1.5 milliseconds.

The analog to digital converter 108 sends, as the signals are converted to digital lead signals, the converted signals to a database 110. In some implementations, the analog to digital converter 108 can send the digital signals to the database 110 via a communication network, such as one or more of: local area network, internet, wide area network, metropolitan area network. Bluetooth network, infrared network, wired network, and any other communication network. The database 110 can store the digital lead signals. The database 110 can be a text file. In other implementations, the database can be a flat-file database, a database management database, and/or a relational database.

A computing device 112 executing a data analysis application can retrieve, at a time after the digital data is stored in the database 110, the digital data from the database 110. The computing device 112 can be one or more of: a desktop computer, a laptop computer, a tablet computer, a cellular/mobile phone, and any other suitable computing device. In some implementations, the computing device 112 can retrieve the digital data from the database 110 via a communication network, such as one or more of: local area network, internet, wide area network, metropolitan area network, Bluetooth network, infrared network, wired network, and any other communication network.

The data analysis application can generate, using the digital signals, depolarization vectors characterizing the lead signals measured during different stages of activity of the patient 104. The data analysis application can determine changes in magnitudes and directions of depolarization vectors during the different stages of activity of the patient 104, such as rest, different stages of exercise, and post exercise. Based on the determined changes in magnitudes and directions of the depolarization vectors, the data analysis application can generate an indication characterizing whether the patient 104 is ischemic, and if yes, an extent and location of myocardial ischemia in the patient 104. The data analysis application can display the extent and location of myocardial ischemia on a graphical user interface executed on the computing device 112.

In some implementations, the leads X, Y, Z, the lead signal amplifiers 106, the analog to digital converter 108, and the computing device can be a part of a vector-cardio-graphic signal analyzer. In one implementation, the vector-cardiographic signal analyzer can optionally also include the database 110.

Figure 2:
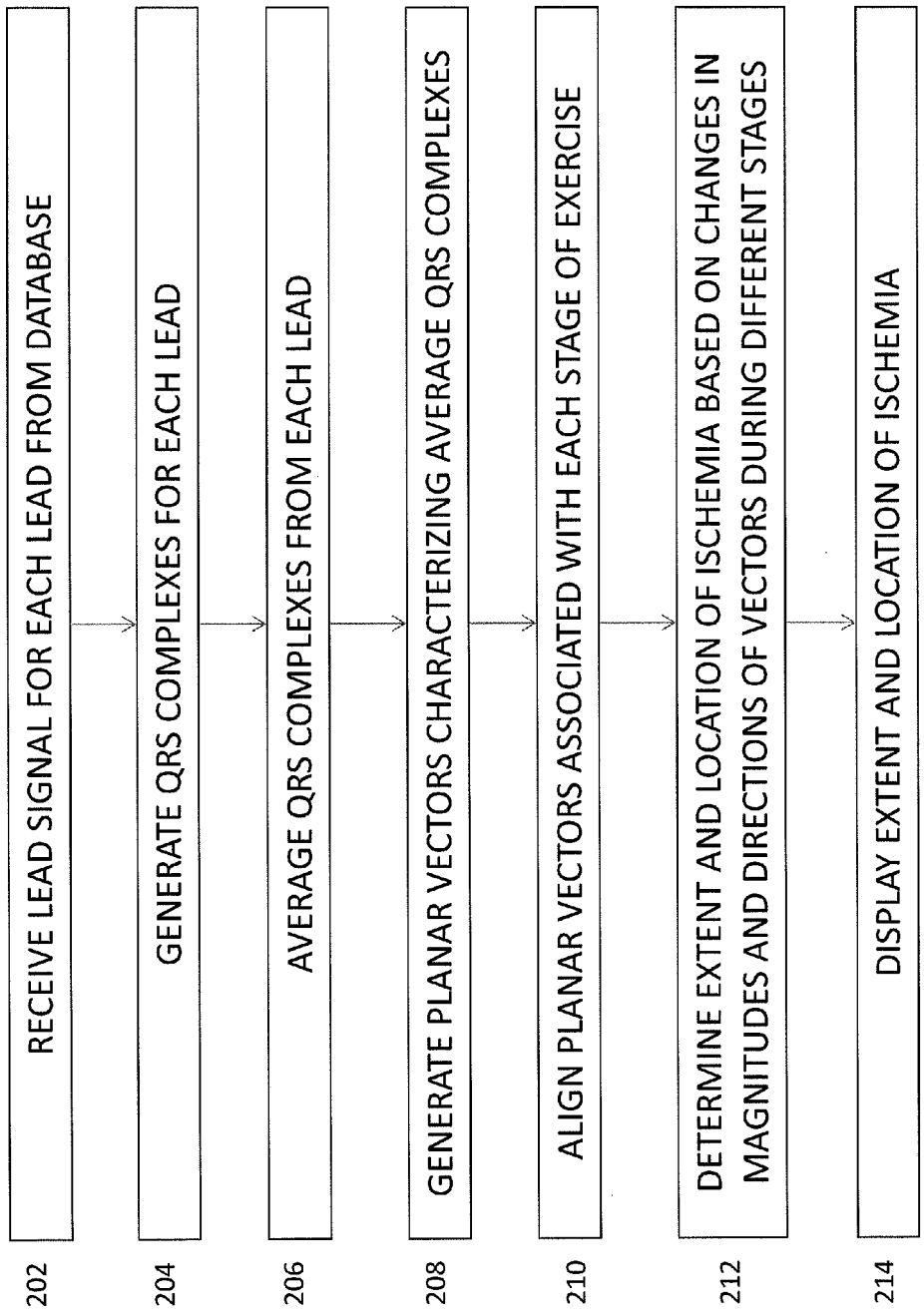
FIG. 2 is a flow-diagram illustrating a generation and display of an extent and location of myocardial ischemia in a patient by a data analysis application executed on the computing device.

FIG. 2 is a flow-diagram 200 illustrating a generation and display of an extent and location of myocardial ischemia in a patient 104 by a data analysis application executed on the computing device 112. The data analysis application can receive, at 202, digital lead signal for each of leads X, Y, and Z from a database 110.

The data analysis application can generate, at 204, a QRS complex for each of leads X, Y, and Z. A QRS complex is a waveform characterizing a depolarization (that is, change in electrical potential) of right and left ventricles of the heart of the patient 104. The generation of the QRS complexes is described in more detail by diagram 300 and diagram 400.

The data analysis application can average, at 206, QRS complexes for each lead X, Y, and Z. To perform this averaging, the data analysis application can execute an averaging algorithm, as described further below. The averaging of the QRS complexes is described in more detail below by diagrams 500 and 600. The averaged QRS complexes can then be aligned, as described in more detail by diagram 700.

The data analysis application can generate, at 208, planar depolarization vectors characterizing average QRS complexes for each lead X, Y, and Z. The data analysis application can generate the planar depolarization vectors for different stages of activity, such as rest, different stages of exercise, and one or more stages of post exercise. These planar depolarization vectors are described in more detail by diagram 800.

The data analysis application can align, at 210, planar depolarization vectors associated with each stage of activity of the patient 104. The "R" wave of the QRS complex associated with the X lead or Y lead for all records of the patient 104 can be used as a point of reference for alignment of the averaged data points representing stages of exercise with the corresponding data points before exercise. The aligned depolarization vectors for before exercise, during exercise, and after exercise are described in more detail by diagram 800 and diagram 900.

The data analysis application can determine changes in magnitudes and directions of depolarization vectors during different stages of activity of the patient 104. In some implementations, comparison algorithms can compare the magnitudes and angles of the planar depolarization vectors at the end of each stage of exercise and after exercise with the vectors occurring at corresponding times before exercise while the patient 104 is in the same posture. Two examples of such a comparison are described in more detail by diagram 1000 and diagram 1100. Based on the determined changes in magnitudes and directions of depolarization vectors, the data analysis application can determine, at 212, extent and location of ischemia in the patient 104 with respect to the stage of exercise.

The data analysis application can display, at 214, the determined extent and location of ischemia on a graphical user interface executed by the computing device 110. One example of such a table is described in more detail by diagram 1300.

Figure 3:
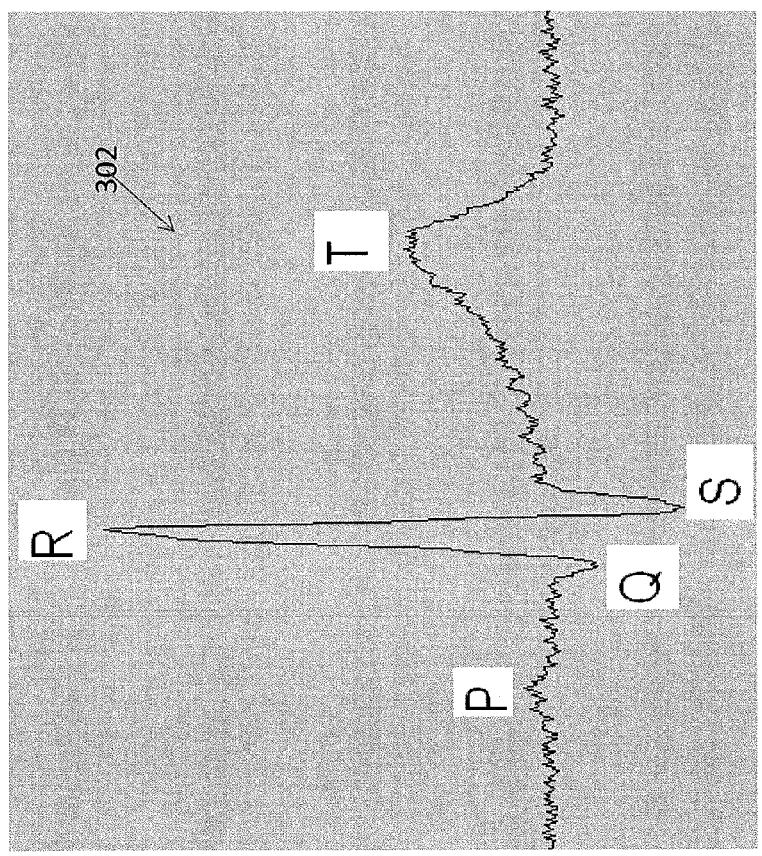
FIG. 3 is a diagram illustrating a QRS complex generated by the data analysis application by using a lead signal obtained from each lead X, Y, and Z.

FIG. 3 is a diagram 300 illustrating a QRS complex 302 generated by the data analysis application by using a lead signal obtained from each lead X, Y, and Z. The QRS waveform can characterize the lead signal.

Figure 4:
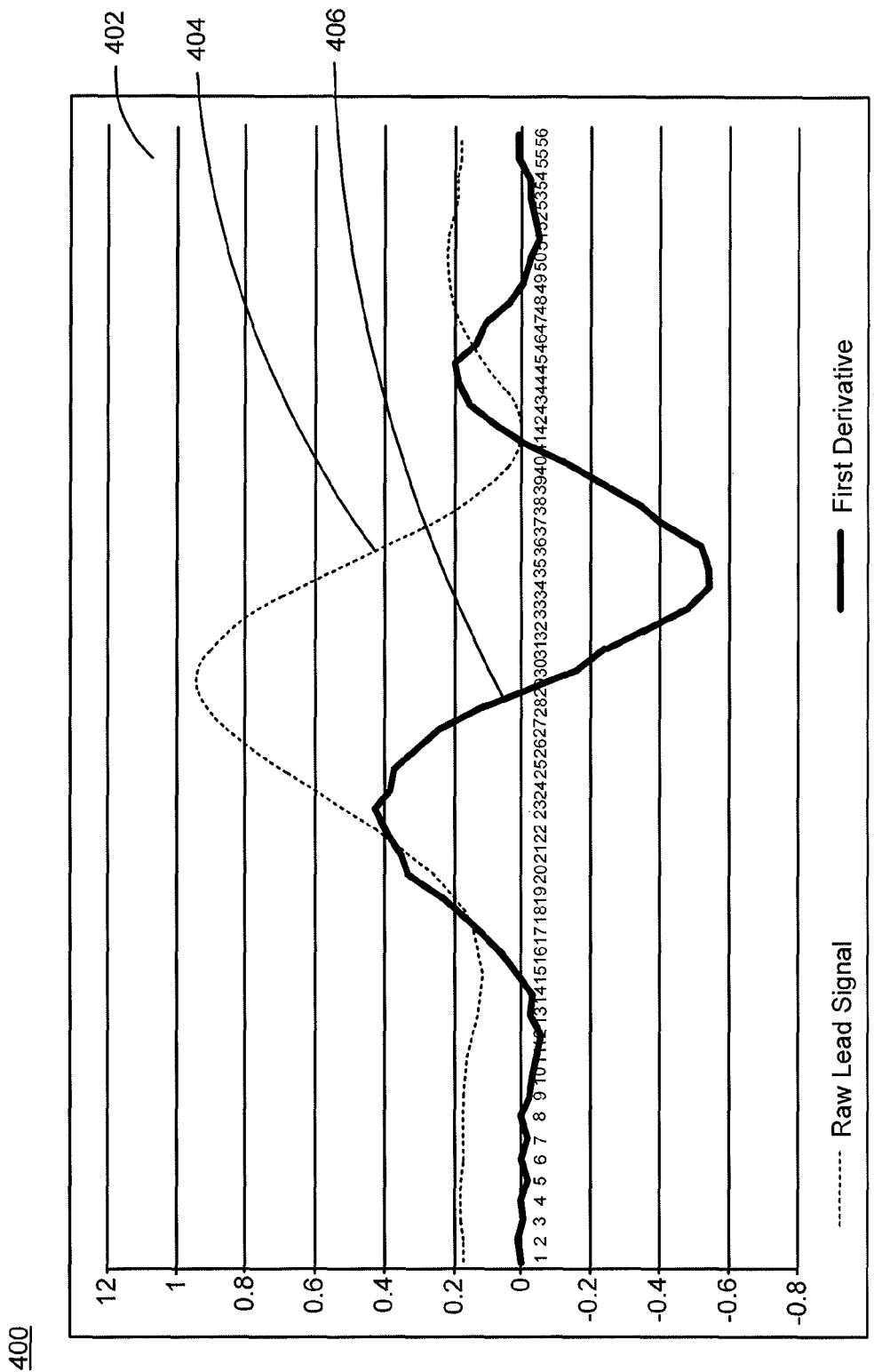
FIG. 4 is a diagram illustrating a QRS complex generated using a lead signal and a first derivative of the lead signal.

FIG. 4 is a diagram 400 illustrating a graph 402 generated by the data analysis application based on main features of the QRS complex 302 obtained from each lead X, Y, and Z. The data analysis application can receive the amplified digital lead signal from the database 110. The graph 402 can display this digital lead signal 404. The data analysis application can compute a first derivative/differential of the digital lead signal 404. The graph 404 can further display the first derivative 406. The first derivative 406 can include some noise, which can correspond to noise originating from movement and electrical activities of muscles underlying the electrodes and/or from radiations in the environment. The data analysis application can then minimize or remove the noise in the first derivative by smoothing the first derivative.

The data analysis application can generate the graph 402 based on main features of the QRS complex 302. For example, a positive peak on the first derivative 406 can mark or correspond to the upward slope of the R wave within the QRS complex 302. Attainment of zero value of the first derivative 406 in transition to a negative trough can mark or correspond to the peak of the R wave. This negative trough of the first derivative 406 can mark or correspond to the downward slope of the R wave.

The first derivative 406 can identify the presence of QRS complex 302 in a window of a raw lead signal being analyzed. Further, the first derivative 406 can mark the associated features, such as beginning and ending positions of the QRS complex 302 and transitions from one signal state to another. For example, the first derivative 406 can accurately determine a position of the R signal peak in the X or Y lead selected for analysis. A positive peak on the first derivative 406 can mark the upward slope of the R wave. Attainment of zero value of the first derivative 406 in transition to a negative trough can mark the peak of the R wave. This negative trough of the first derivative 406 can mark the downward slope of the R wave.

The upstroke of the peak, the down stroke of the trough, and the interval between the peak and trough can identify the presence of QRS complex 302 by applying one or more rule sets. A fixed interval before and after the zero point can mark a window of the raw lead signal that is to be analyzed.

Figure 5:
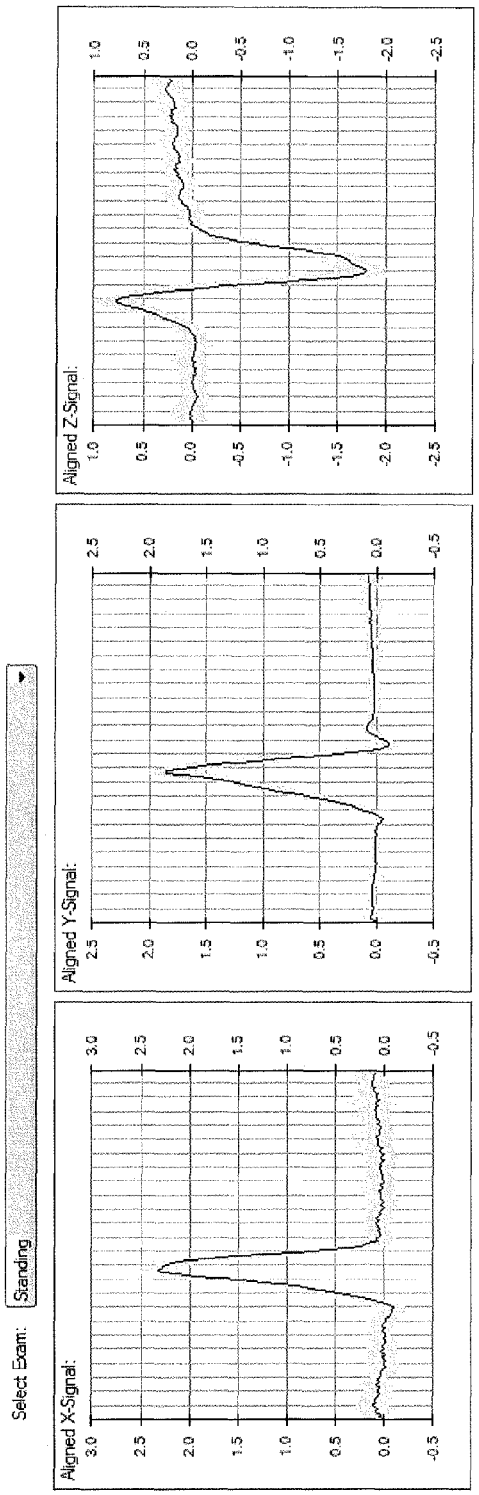
FIG. 5 is a diagram illustrating averaged of successive QRS complexes before a patient begins exercise.

FIG. 5 is a diagram 500 illustrating averaged successive QRS complexes before a patient 104 begins exercise. Before exercise, the lead signals at leads X, Y, and Z are obtained every 1.5 milliseconds. Each lead signal obtained every 1.5 milliseconds can correspond to a different window of analysis, wherein each window can correspond to a respective QRS complex. After each unique QRS complex has been identified, the data analysis application can execute a cross-correlation technique to align successive QRS complexes for averaging. The data analysis application can then average the aligned QRS complexes. This cross-correlation and averaging technique is described in more detail below.

Initially, a current QRS complex can be used as a reference/baseline QRS complex. The data analysis application can sample the current QRS complex to obtain voltage values recorded at a few (for example, ten to fourteen) sampled time points associated with the current QRS complex.

Subsequently, the data analysis application can sample a first subsequent QRS complex of the next time window to obtain voltage values recorded at corresponding few (for example, ten to fourteen) sampled time points associated with the first subsequent QRS complex. Next, the data analysis application can calculate a cross-correlation between the current QRS complex and the first subsequent QRS complex. The cross-correlation can characterize similarity between the current QRS complex and a first subsequent QRS complex, which has a time-lag as it is in a subsequent time window. The cross-correlation can be evaluated as a sum of products of voltage values of each of the current QRS complex and the first subsequent QRS complex can be calculated in accordance with the mathematical equation:

$$(f * g)[n] \overset{def}{=} \sum_{m=-\infty}^{\infty} f^*[m]g[n+m].,$$

wherein: f is a complex conjugate of the current QRS complex, g is the first subsequent QRS complex, and n and m are sampled values (for example, integer values) of time.

Further, the data analysis application can sample a second subsequent QRS complex, and can compute a cross-correlation between the current QRS complex and the second subsequent QRS complex of another next time window. The cross-correlation can characterize similarity between the current QRS complex and the second subsequent QRS complex. The cross-correlation can be evaluated as a sum of products of voltage values of each of the current QRS complex and the second subsequent QRS complex. Similarly, the data analysis application can compute a cross-correlation between the current QRS complex and each subsequent QRS complex to determine corresponding sums of multiplication products.

Next, the data analysis application can compare all the different computed cross-correlations by comparing the respective sums of products with each other so as to determine the highest computed cross-correlation. The highest computed cross-correlation can indicate a particular subsequent QRS complex, shape and amplitude of which are most similar to shape and amplitude of the current QRS complex. Now, the current QRS complex and the particular QRS complex associated with the highest computed cross-correlation are aligned for averaging.

Further, the data analysis application can average QRS complex and the particular QRS complex associated with the highest computed cross-correlation to generate an averaged QRS complex. Now, this averaged QRS complex can be used as a reference/baseline QRS complex. The data analysis application can again calculate a sum of multiplication products of the sampled QRS complex. The highest sum of multiplication products can indicate another QRS complex. The reference/baseline QRS complex can then be averaged with this indicated QRS complex to generate another averaged QRS complex, which can be used as a reference/baseline QSR complex in a subsequent iteration.

This process of computing cross-correlation, determining highest cross-correlation, and averaging can be repeated for a threshold number of times or iterations. The variance between the maximum sum of products of a sampled QRS complex and the evolving average QRS complex can be checked in each iteration. If the variance exceeds a threshold value, the QRS complex (other than the reference/baseline QSR complex) can be excluded from the averaging process.

The final result of the repetitions/iterations noted above can be a display of a consistent and an averaged QRS complex and associated variations in values of the data points. The averages of the data points of the X, Y and Z lead signals can be used to determine magnitudes and directions of associated vectors in the orthogonal planes (for example, horizontal plane, frontal plane, and sagittal plane). The averaged X, Y and Z signals can represent consistent characteristics of ventricular depolarization during the respective stages of the exercise.

Figure 6:
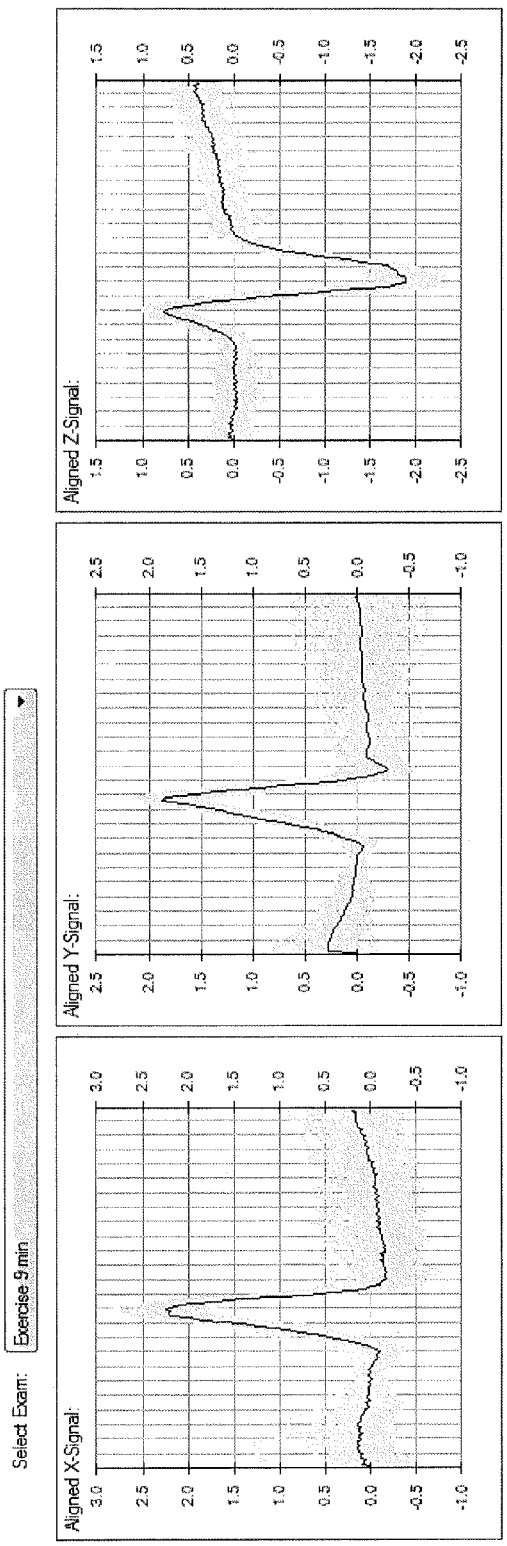
FIG. 6 is a diagram illustrating averaged successive QRS complexes of lead signals at leads X, Y, and Z during a predetermined time of exercise.

FIG. 6 is a diagram 600 illustrating averaged successive QRS complexes of lead signals at leads X, Y, and Z during a predetermined time (for example, 9 minutes) of exercise. The averaging is performed as described above.

Figure 7:
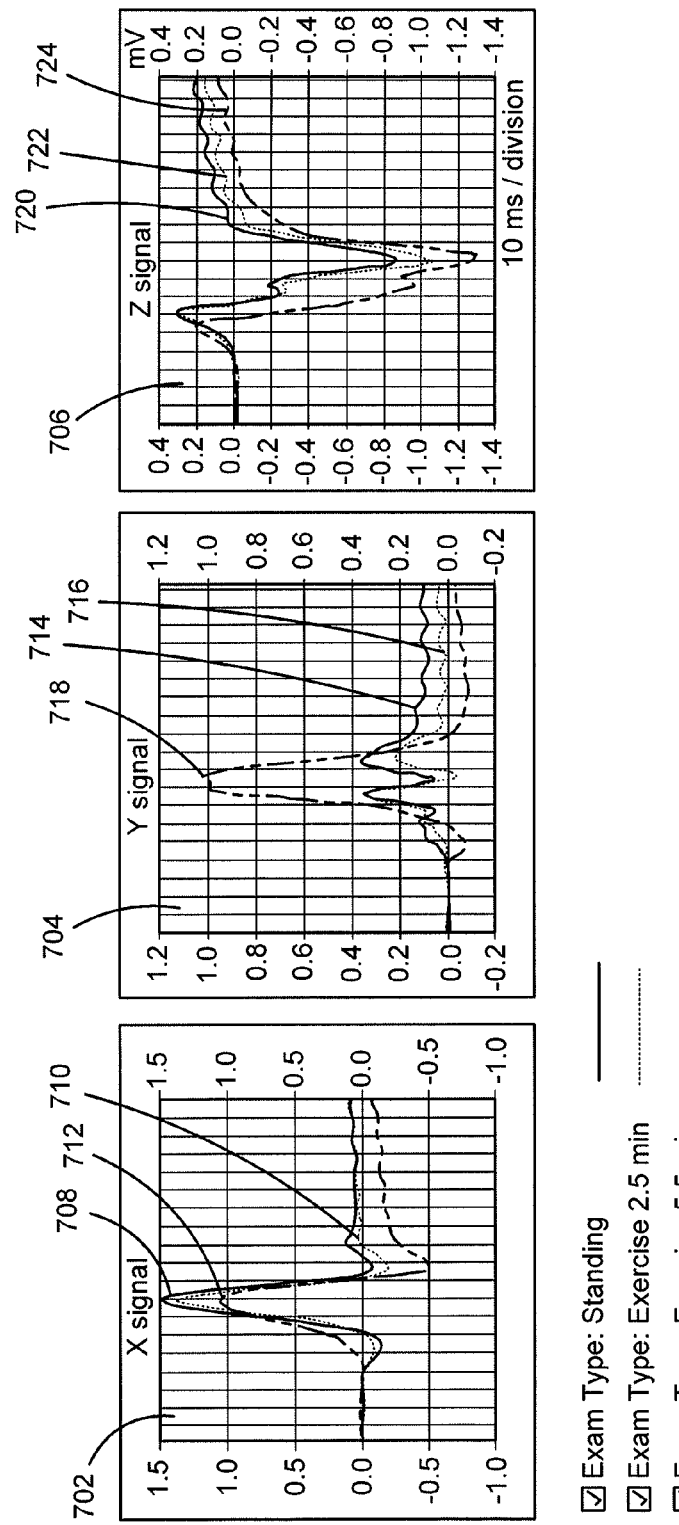
FIG. 7 is a diagram illustrating an alignment of average orthogonal lead signals at leads X, Y, and Z during rest, during a first time since beginning of exercise, and during a second time since the beginning of exercise.

FIG. 7 is a diagram 700 illustrating an alignment of average orthogonal lead signals at leads X, Y, and Z during rest, during a first time (more specifically, 2.5 minutes) since beginning of exercise, and during a second time (more specifically, 5 minutes) since the beginning of exercise. Such an alignment can be used to analyze QRS complex changes induced by exercise. The diagram 700 can include a graph 702, a graph 704, and a graph 706.

The graph 702 can display averaged QRS complexes for a lead signal in the X lead. These QRS complexes can include: an averaged QRS complex 708 obtained when the patient 104 is at rest, an average QRS complex 710 when the patient 104 has been exercising for the first time (that is, 2.5 minutes), and an averaged QRS complex 712 obtained when the patient 104 has been exercising for the second time (that is, 5.5 minutes).

The graph 704 can display averaged QRS complexes for a lead signal in the Y lead. These QRS complexes can include: an averaged QRS complex 714 obtained when the patient 104 is at rest, an average QRS complex 716 when the patient 104 has been exercising for the first time (that is, 2.5 minutes), and an averaged QRS complex 718 obtained when the patient 104 has been exercising for the second time (that is, 5.5 minutes).

The graph 706 can display averaged QRS complexes for a lead signal in the Z lead. These QRS complexes can include: an averaged QRS complex 720 obtained when the patient 104 is at rest, an average QRS complex 722 when the patient 104 has been exercising for the first time (that is, 2.5 minutes), and an averaged QRS complex 724 obtained when the patient 104 has been exercising for the second time (that is, 5.5 minutes).

Figure 8:
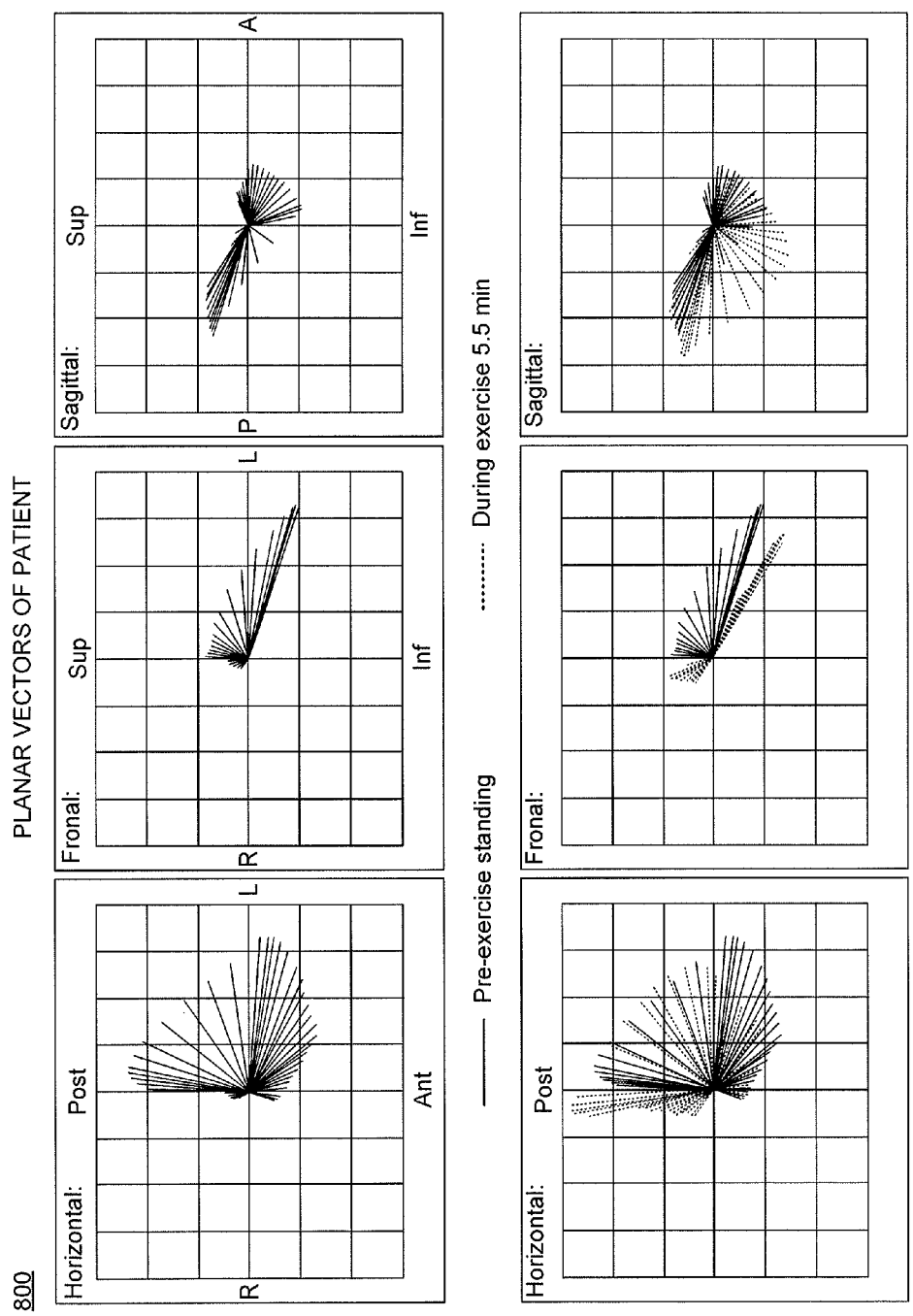
FIG. 8 is a diagram illustrating depolarization vectors in three orthogonal planes generated using respective average QRS complexes before exercise and aligned with corresponding vectors during exercise.

FIG. 8 is a diagram 800 illustrating depolarization vectors generated using respective average QRS complexes 708, 710, 712, 714, 716, 718, 720, 722, 724, and QRS complexes for time-after-exercise. The data analysis application can align these depolarization vectors for measurement and display of changes induced by exercise. Note that diagram 800 is an exemplary figure specific for a patient that may have been different from the patient associated with diagram 700.

Figure 9:
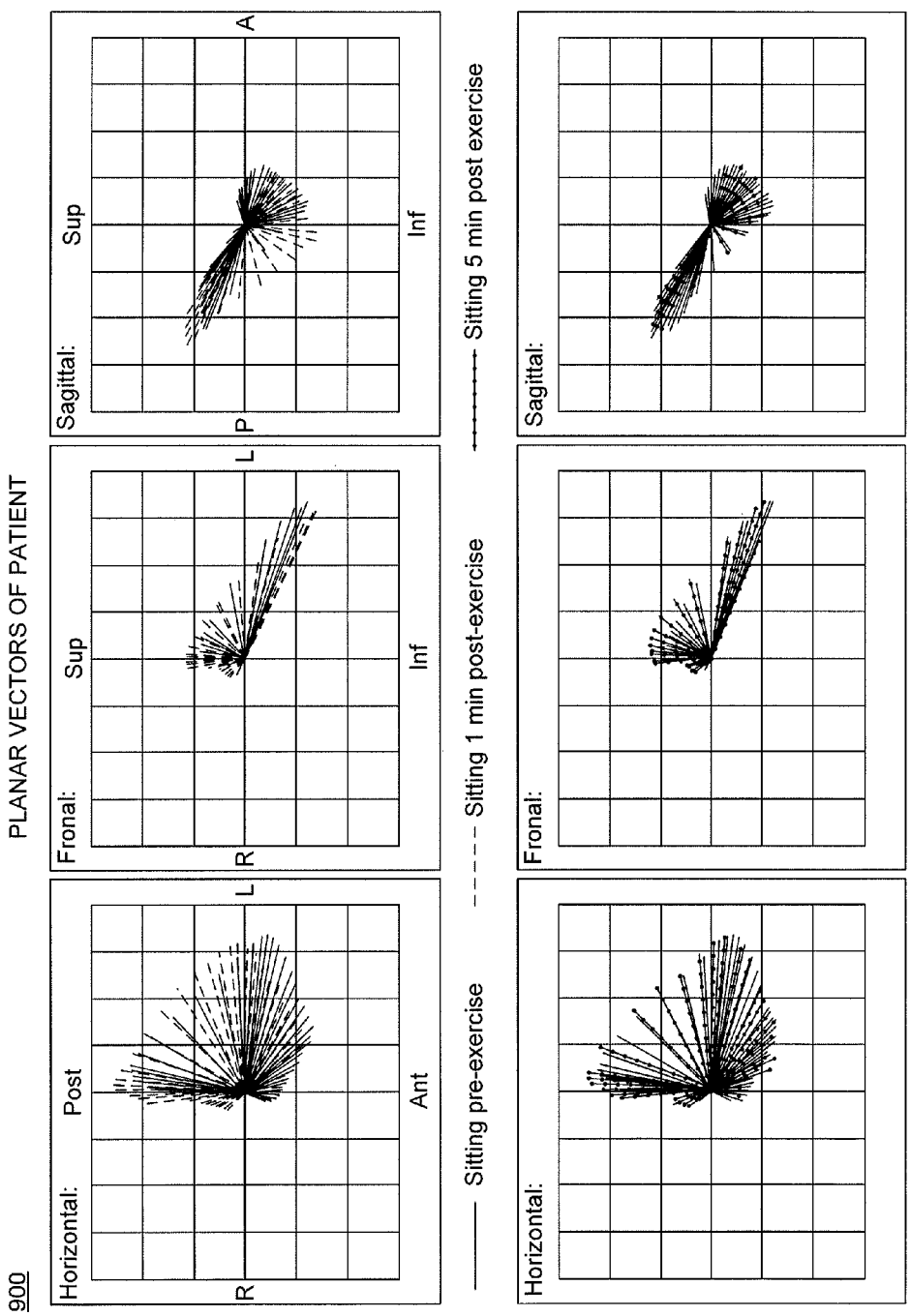
FIG. 9 is a diagram illustrating aligned depolarization vectors before and two intervals after exercise showing resolution of changes in magnitude and direction of exercise illustrated in FIG. 8.

FIG. 9 is a diagram 900 illustrating aligned depolarization vectors for before exercise, during exercise, and after exercise. Note that diagram 900 is an exemplary figure specific for a patient that may have been same as patient associated with diagram 800 but different from the patient associated with diagram 700.

During experiments, both the patient associated with diagram 700 and the patient associated with diagrams 800 and 900 showed the illustrated changes in the sequence of depolarization associated with changes in vector magnitude. In some implementations, the reduction in vector magnitude can be more marked in the horizontal plane and can be less marked (yet easily seen) in frontal plane and sagittal plane, as shown in diagrams 800 and 900. In one implementation, the resolution at five minutes after exercise can be more complete, as shown in diagrams 800 and 900. Thus, consistency of alignment of planar vectors enables comparison of vector magnitude and direction during and after exercise with the condition before exercise.

Figure 10:
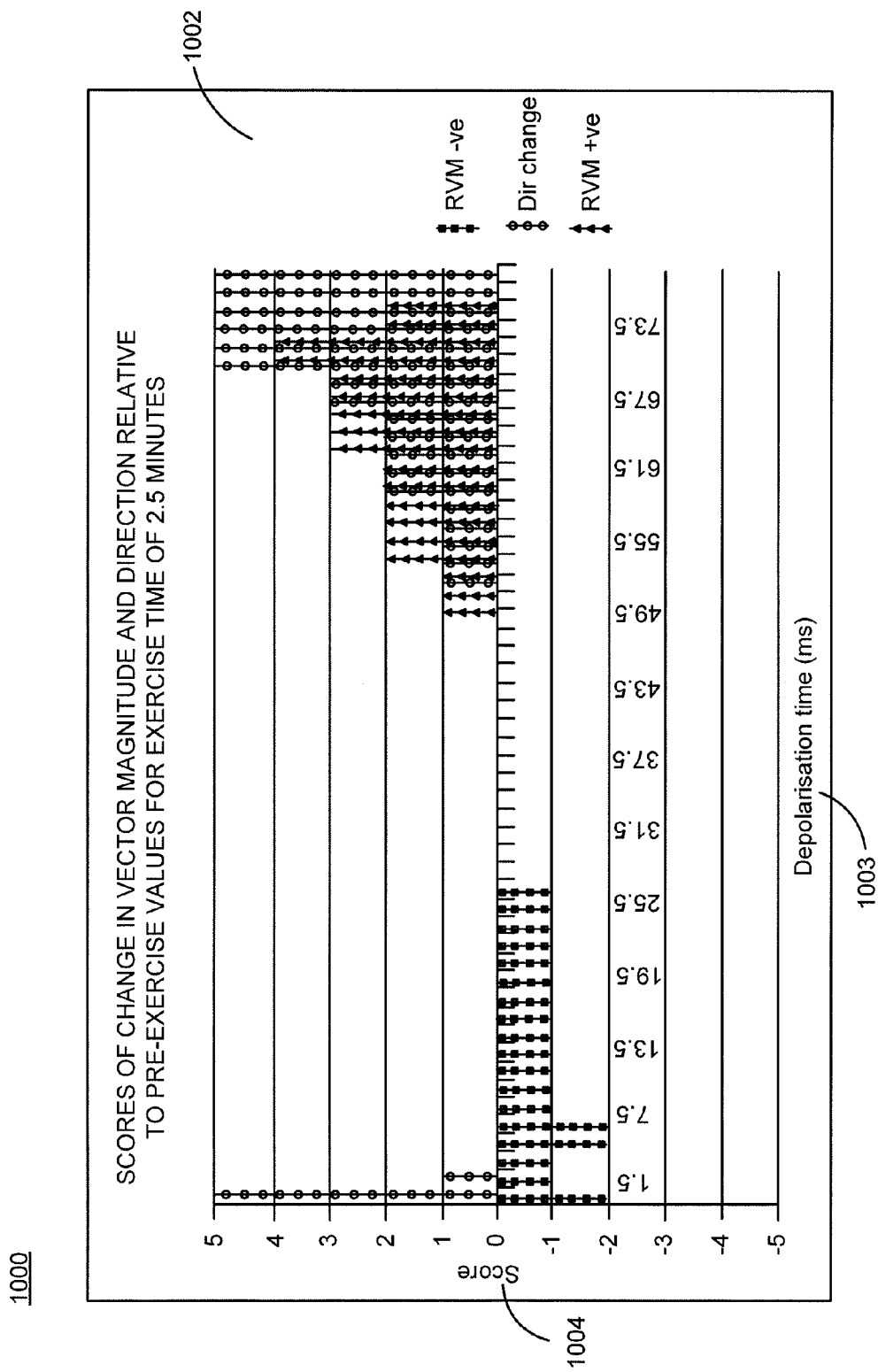
FIG. 10 is a diagram illustrating a graph showing a comparison of vector magnitudes and directions at a particular time since beginning of exercise with a comparison of vector magnitudes and directions before exercise.

FIG. 10 is a diagram 1000 illustrating a graph 1002 showing a comparison of vector magnitudes and directions at a particular time (more specifically, 2.5 minutes) since beginning of exercise with a comparison of vector magnitudes and directions before exercise. The data analysis application can generate the graph 1002 on a graphical user interface generated on the computing device 110. At each discrete point of depolarization time 1003, a relative vector magnitude (RVM) is calculated to be a ratio of vector magnitude at the particular time to the vector magnitude before exercise. This ratio characterizes a score 1004 associated with the RVM. The RVM can be one of an enhanced RVM (when RVM is more than one), a reduced RVM (when RVM is less than one), and an unchanged RVM.

If the average difference between the planar angles of a vector at a particular time and the planar angles of the vector at the same time before exercise exceeds 10° then, a score 1004 associated with change in direction can be shown in the graph 1002 with a particular color (for example, red), which can indicate the change in vector direction at the particular point of depolarization time 1003. For a change in direction by ten degrees, the score 1004 associated with direction can be one.

Figure 11:
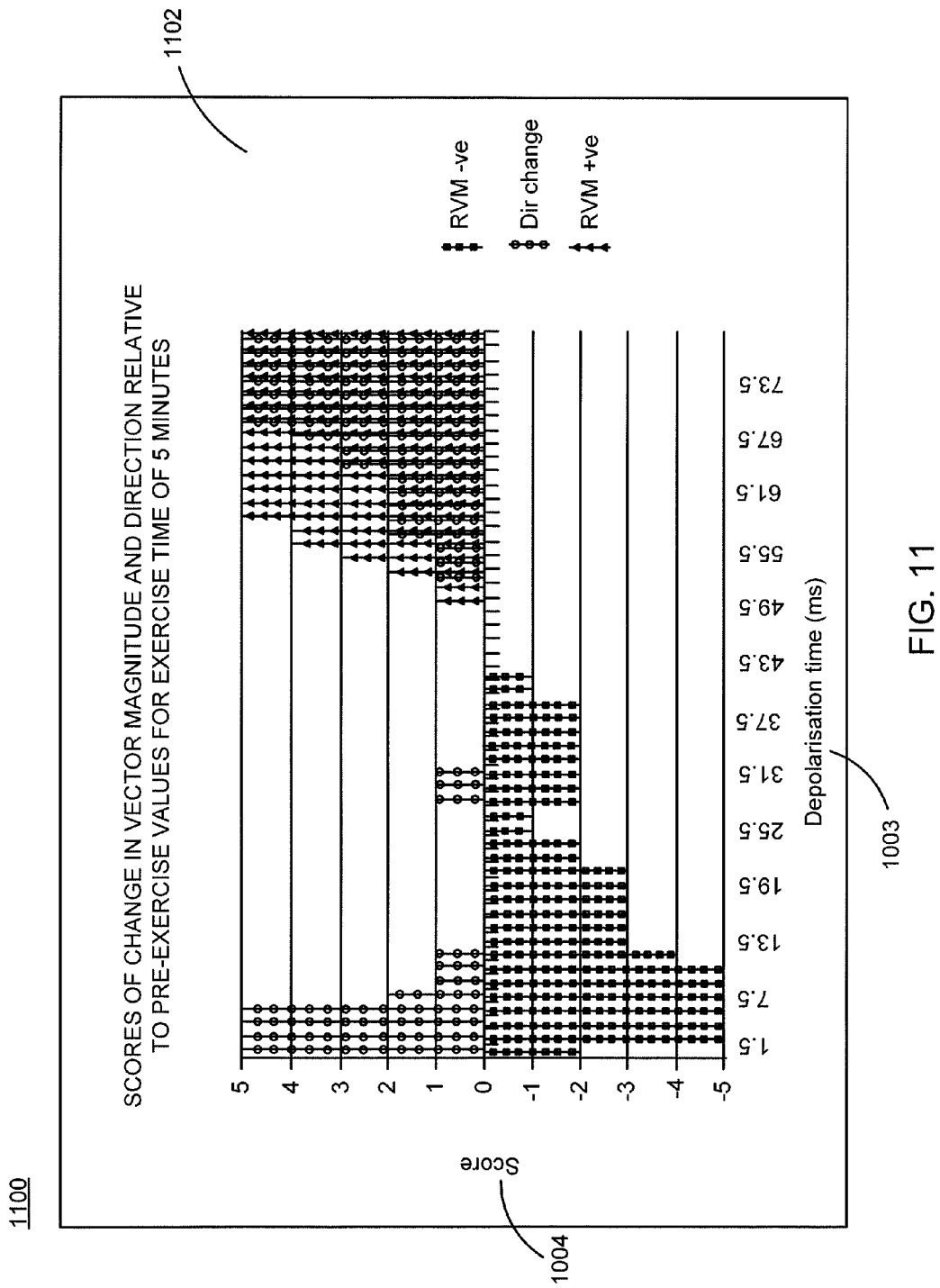
FIG. 11 is a diagram illustrating a graph showing a comparison of vector magnitudes and directions at another time since beginning of exercise with a comparison of vector magnitudes and directions before exercise.

FIG. 11 is a diagram 1100 illustrating a graph 1102 showing a comparison of vector magnitudes and directions at another time (more specifically, 5 minutes) since beginning of exercise with a comparison of vector magnitudes and directions before exercise. The data analysis application can generate the graph 1102 on a graphical user interface executed on the computing device 110.

Figure 12:
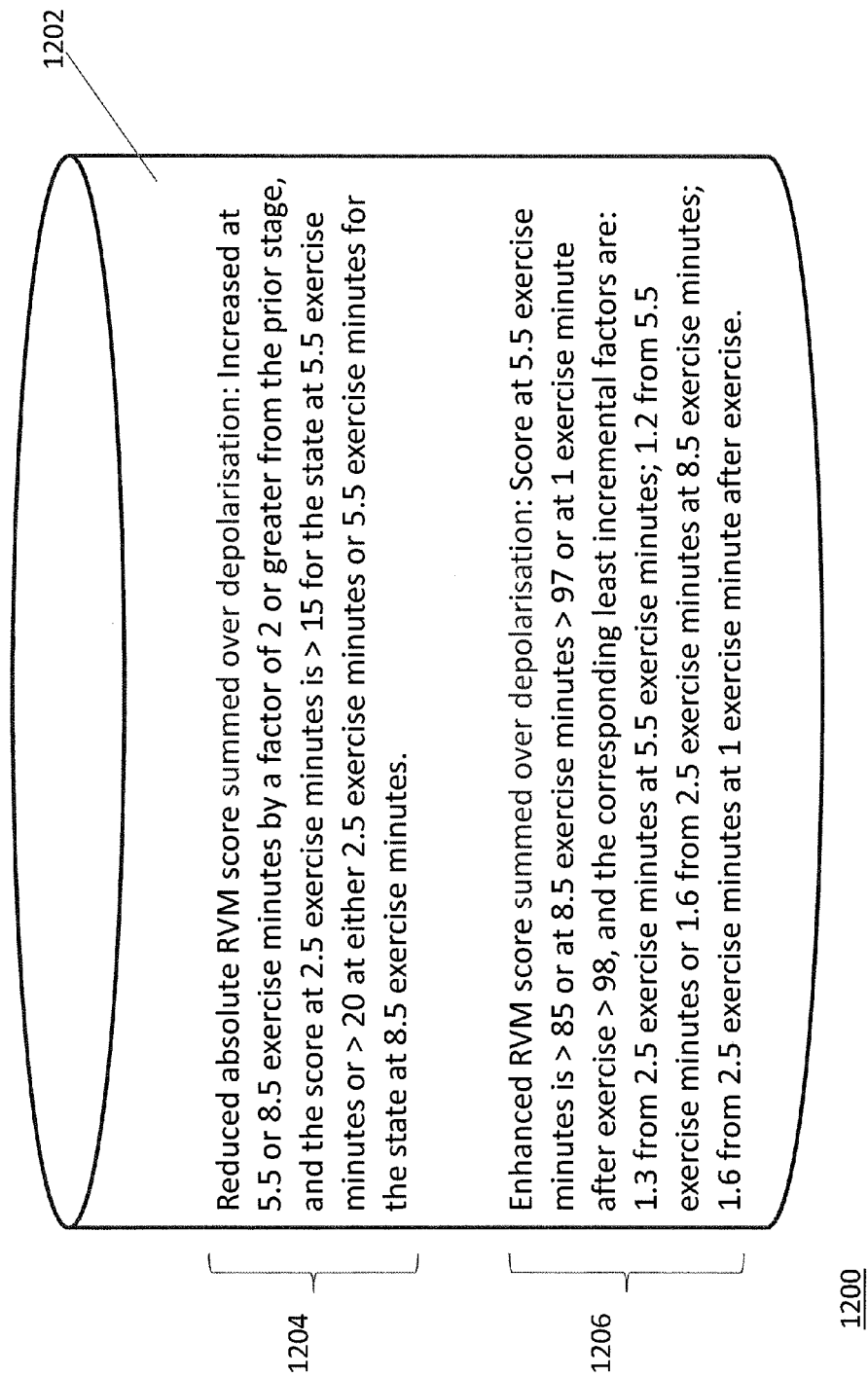
FIG. 12 is a diagram illustrating a database including criteria for identifying signs of ischemia in a patient.

FIG. 12 is a diagram 1200 illustrating a database 1202 including criteria for identifying signs of ischemia in a patient 104. The database 1202 can be a table, a text file, a flat-file database, a database management database, and/or a relational database. The database 1202 can include criteria 1204 and 1206. The rules 1202 and 1204 have been generated based on experiments performed on historical data of a plurality (for example, hundreds or thousands) of patients. If the patient 104 satisfies at least one of the criteria 1204 and 1206, the patient 104 is diagnosed to have signs of ischemia. The criteria 1204 and 1206 are described in more detail below.

During exercise, relative vector magnitudes (RVMs) associated with individuals with or without ischemia generally tend to reduce during the initial forty milliseconds of depolarization and to enhance in the later forty milliseconds. Change in the average planar vector magnitude relative to its value before exercise can be scored. Sums of scores of reduced RVM and enhanced RVM during depolarization can indicate, by using criteria 1204 and 1206, patients with ischemia. The criteria 1204 and 1206 are examples based on a particular set of historic data. The criteria 1204 and 1206 can vary based on a different set of historic data when the number of individuals in the plurality of individuals changes significantly.

Criteria 1204—Reduced absolute RVM score summed over depolarisation: Increased at 5.5 or 8.5 exercise minutes by a factor of 2 or greater from the prior stage, and the score at 2.5 exercise minutes is >15 for the state at 5.5 exercise minutes or >20 at either 2.5 exercise minutes or 5.5 exercise minutes for the state at 8.5 exercise minutes.

Criteria 1206 Enhanced RVM score summed over depolarisation: Score at 5.5 exercise minutes is >85 or at 8.5 exercise minutes >97 or at 1 exercise minute after exercise >98, and the corresponding least incremental factors are: 1.3 from 2.5 exercise minutes at 5.5 exercise minutes; 1.2 from 5.5 exercise minutes or 1.6 from 2.5 exercise minutes at 8.5 exercise minutes; 1.6 from 2.5 exercise minutes at 1 exercise minute after exercise.

If the patient 104 is diagnosed to have signs of ischemia, the sum of RVM scores 1004 and span of contiguous vectors with reduced RVM as well as the stage of exercise when the criteria of ischaemia are met can provide a measure of extent of ischemia. Further, if the patient 104 is diagnosed to have signs of ischemia, the location of ischemia can be characterized by an anatomical structure in the direction of the depolarization vector before exercise; the direction being interpreted in relation to a virtual point of reference at the intersection of the three orthogonal axes located in the left ventricle approximately 25% of the length from apex to the aortic valve. The direction (for example, clockwise or anti-clockwise) of change in direction of vectors can assist by indicating the general location of ischemia.

FIG. 13 is a diagram 1300 illustrating a summary of changes in the magnitude of vectors relative to the corresponding values before exercise (RVM) and changes in direction of planar vectors, both represented by scores, at different times during depolarisation at 8.5 minutes of exercise for comparison with other times during and after exercise. For vectors reduced in magnitude, the extent can be indicated by the duration of contiguous vectors and the individual and sum of associated scores. The spatial location of reduction in electromotive forces (EMF) that affected the vectors can be determined based on the direction of vectors before exercise and inferred from the nature of change in direction of vectors reduced in RVM. The location can be indicated as main and lesser directions. Affected structures of the heart can be inferred from the main directions of affected vectors before exercise that can generally be depolarized at the times indicated by reduction in RVM. Templates can be used to process the data characterizing changes in magnitude and direction of vectors so as to indicate extent, duration, and spatial direction of affected vectors.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language.

As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device, such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, Bluetooth network, infrared network, or other networks.

Although a few variations have been described in detail above, other modifications can be possible. For example, the logic flows depicted in the accompanying figures and described herein do not require the particular order shown, or sequential order, to achieve desirable results. Other embodiments may be within the scope of the following claims.

What is claimed is:

1. A method comprising:
receiving, by a data analysis application executed on a computing device, digital lead signals characterizing a digitized form of lead signals obtained from a plurality of leads connected to electrodes attached on a body of a patient, the lead signals characterizing components of a collective signal in corresponding orthogonal planes;
constructing, by the data analysis application and using the digital lead signals, QRS complexes associated with the corresponding orthogonal planes, the constructing of the QRS complexes comprising:
receiving a digital lead signal of the lead signals;
generating a first differential of the lead signal;
removing high frequency noise from the lead signal by using a low pass filter to obtain a smooth first differential; and
simultaneously displaying the digital lead signal and the first differential to identify parameters of the QRS complex associated with the digital lead signal, the parameters being used to construct the QRS complex;
generating, by the data analysis application, planar vectors associated with averages of the QRS complexes;
displaying, by the data analysis application and on a graphical user interface executed by the computing device, an indication characterizing extent and location of myocardial ischemia in the body of the patient, the indication being generated based on changes in magnitudes and directions of the planar vectors during different stages of activity of the patient.

2. The method of claim 1, wherein:
a positive peak of the smooth first differential identifies an upward slope of R wave in the QRS complex associated with the digital lead signal;
attainment of zero value of the first differential in transition to a negative trough identifies a peak of the R wave in the QRS complex; and
a negative trough of the first differential identifies a downward slope of the R wave in the QRS complex.

3. A method comprising:
receiving, by a data analysis application executed on a computing device, digital lead signals characterizing a digitized form of lead signals obtained from a plurality of leads connected to electrodes attached on a body of a patient, the lead signals characterizing components of a collective signal in corresponding orthogonal planes;
constructing, by the data analysis application and using the digital lead signals, QRS complexes associated with the corresponding orthogonal planes;
generating, by the data analysis application, planar vectors associated with averages of the QRS complexes, the averages of the QRS complexes being obtained by performing an averaging of the QRS complexes, the averaging comprising:
calculating a baseline characterizing a mean value of sample points of PR segment preceding each QRS complex;
adjusting a digital lead signal of the lead signals with reference to the baseline to obtain a baseline adjusted lead signal;
separately cross-correlating the baseline adjusted lead signal with a plurality of lead signals in subsequent windows of analysis, each cross-correlation resulting in a sum of products of values of the baseline adjusted lead signal and a corresponding lead signal of a subsequent window of analysis;
determining, from the plurality of lead signals in subsequent windows of analysis, a lead signal that has a highest sum of corresponding products, the determined lead signal with the highest sum of corresponding products being more similar to the baseline adjusted lead signal than other lead signals; and
averaging a QRS complex associated with the baseline adjusted lead signal and a QRS complex associated with the determined lead signal with the highest sum of corresponding products when the QRS complex associated with the determined lead signal is determined to be a regular waveform; and
displaying, by the data analysis application and on a graphical user interface executed by the computing device, an indication characterizing extent and location of myocardial ischemia in the body of the patient, the indication being generated based on changes in magnitudes and directions of the planar vectors during different stages of activity of the patient.

4. A method comprising:
receiving, by a data analysis application executed on a computing device, digital lead signals characterizing a digitized form of lead signals obtained from a plurality of leads connected to electrodes attached on a body of a patient, the lead signals characterizing components of a collective signal in corresponding orthogonal planes;

constructing, by the data analysis application and using the digital lead signals, QRS complexes associated with the corresponding orthogonal planes;

generating, by the data analysis application, planar vectors associated with averages of the QRS complexes;

displaying, by the data analysis application and on a graphical user interface executed by the computing device, an indication characterizing extent and location of myocardial ischemia in the body of the patient, the indication being generated based on changes in magnitudes and directions of the planar vectors during different stages of activity of the patient, the generating of the indication of extent and location of myocardial ischemia comprising:

generating a relative vector magnitude at each depolarization time point at a first time since the patient started an exercise, the relative vector magnitude being a ratio of vector magnitude at the first time to the vector magnitude before exercise; and using criteria to generate an indication that the patient has ischemia.

5. A non-transitory computer program product storing instructions that, when executed by at least one programmable processor, cause the at least one programmable processor to perform operations comprising:

receiving, by a data analysis application executed on a computing device, digital lead signals characterizing a digitized form of lead signals obtained from a plurality of leads connected to electrodes attached on a body of a patient, the lead signals characterizing components of a collective signal in corresponding orthogonal planes;

constructing, by the data analysis application and using the digital lead signals, QRS complexes associated with the corresponding orthogonal planes, the constructing of the QRS complexes comprising:

receiving, at the data analysis application, a digital lead signal of the lead signals;

generating, by the data analysis application, a first differential of the lead signal;

removing, by the data analysis application, high frequency noise from the lead signal by using a low pass filter to obtain a smooth first differential; and simultaneously displaying, by the data analysis application and on the graphical user interface, the digital lead signal and the first differential to identify parameters of the QRS complex associated with the digital lead signal, the parameters being used to construct the QRS complex;

generating, by the data analysis application, planar vectors associated with averages of the QRS complexes; and displaying, by the data analysis application and on a graphical user interface executed by the computing device, an indication characterizing extent and location of myocardial ischemia in the body of the patient, the indication being generated based on changes in magnitudes and directions of the planar vectors during different stages of activity of the patient.

6. The computer program product of claim 5, wherein:

a positive peak of the smooth first differential identifies an upward slope of R wave in the QRS complex associated with the digital lead signal;

attainment of zero value of the first differential in transition to a negative trough identifies a peak of the R wave in the QRS complex; and a negative trough of the first differential identifies a downward slope of the R wave in the QRS complex.

7. A non-transitory computer program product storing instructions that, when executed by at least one programmable processor, cause the at least one programmable processor to perform operations comprising:

receiving, by a data analysis application executed on a computing device, digital lead signals characterizing a digitized form of lead signals obtained from a plurality of leads connected to electrodes attached on a body of a patient, the lead signals characterizing components of a collective signal in corresponding orthogonal planes;

constructing, by the data analysis application and using the digital lead signals, QRS complexes associated with the corresponding orthogonal planes;

generating, by the data analysis application, planar vectors associated with averages of the QRS complexes, the averages of the QRS complexes being is obtained by performing an averaging of the QRS complexes, the averaging comprising:

calculating a baseline characterizing a mean value of sample points of PR segment preceding each QRS complex;

adjusting a digital lead signal of the lead signals with reference to the baseline to obtain a baseline adjusted lead signal;

separately cross-correlating the baseline adjusted lead signal with a plurality of lead signals in subsequent windows of analysis, each cross-correlation resulting in a sum of products of values of the baseline adjusted lead signal and a corresponding lead signal of a subsequent window of analysis;

determining, from the plurality of lead signals in subsequent windows of analysis, a lead signal that has a highest sum of corresponding products, the determined lead signal with the highest sum of corresponding products being more similar to the baseline adjusted lead signal than other lead signals; and averaging a QRS complex associated with the baseline adjusted lead signal and a QRS complex associated with the determined lead signal with the highest sum of corresponding products when the QRS complex associated with the determined lead signal is determined to be a regular waveform; and displaying, by the data analysis application and on a graphical user interface executed by the computing device, an indication characterizing extent and location of myocardial ischemia in the body of the patient, the indication being generated based on changes in magnitudes and directions of the planar vectors during different stages of activity of the patient.

8. A non-transitory computer program product storing instructions that, when executed by at least one programmable processor, cause the at least one programmable processor to perform operations comprising:

receiving, by a data analysis application executed on a computing device, digital lead signals characterizing a digitized form of lead signals obtained from a plurality of leads connected to electrodes attached on a body of a patient, the lead signals characterizing components of a collective signal in corresponding orthogonal planes;

constructing, by the data analysis application and using the digital lead signals, QRS complexes associated with the corresponding orthogonal planes;

generating, by the data analysis application, planar vectors associated with averages of the QRS complexes;

displaying, by the data analysis application and on a graphical user interface executed by the computing device, an indication characterizing extent and location of myocardial ischemia in the body of the patient, the indication being generated based on changes in magnitudes and directions of the planar vectors during different stages of activity of the patient, the generating of the indication of extent and location of myocardial ischemia comprising:

generating a relative vector magnitude at each depolarization time point at a first time since the patient started an exercise, the relative vector magnitude being a ratio of vector magnitude at the first time to the vector magnitude before exercise; and using criteria to generate an indication that the patient has ischemia.

* * * * *